(12) United States Patent
Konetschny et al.

(10) Patent No.: US 7,612,872 B2
(45) Date of Patent: Nov. 3, 2009

(54) METHOD OF DETERMINING THE FLATNESS OF A FOUNDATION TO WHICH A BUILDING STRUCTURE, MACHINERY OR EQUIPMENT IS TO BE MOUNTED

(75) Inventors: Volker Konetschny, Munich (DE); Klaus Stroel, Munich (DE)

(73) Assignee: Prueftechnik Dieter Subsch AG, Ismaning (DE)

( * ) Notice: Subject to any disclaimer, the term of this patent is extended or adjusted under 35 U.S.C. 154(b) by 241 days.

(21) Appl. No.: 11/680,952

(22) Filed: Mar. 1, 2007

(65) Prior Publication Data
US 2008/0212065 A1    Sep. 4, 2008

(51) Int. Cl.
*G01C 3/08*    (2006.01)
(52) U.S. Cl. ...................... 356/5.01; 356/4.01
(58) Field of Classification Search ........... None
See application file for complete search history.

(56) References Cited

U.S. PATENT DOCUMENTS

| | | | |
|---|---|---|---|
| 3,687,556 | A | 8/1972 | Price et al. |
| 4,936,678 | A | 6/1990 | Gordon et al. |
| 6,172,742 | B1 | 1/2001 | Yamazaki |
| 6,259,110 | B1 * | 7/2001 | Ettinger et al. ............ 356/400 |
| 7,110,092 | B2 | 9/2006 | Kasper et al. |
| 7,115,852 | B2 | 10/2006 | Ohtomo et al. |

FOREIGN PATENT DOCUMENTS

| | | |
|---|---|---|
| EP | 0 661 520 A1 | 7/1995 |
| EP | 1 632 785 A1 | 3/2006 |
| GB | 2 090 096 A | 6/1982 |
| GB | 2 173 369 A | 10/1986 |
| WO | 02 10681 A1 | 2/2002 |

OTHER PUBLICATIONS

International Search Report for International Application No. PCT/EP2008/001633, Jun. 2008.

* cited by examiner

*Primary Examiner*—Michael A Lyons
*Assistant Examiner*—Juan D Valentin
(74) *Attorney, Agent, or Firm*—David S. Safran; Roberts Mlotkowski Safran & Cole, P.C.

(57) ABSTRACT

A method for measuring flatness of a factory floor upon which machinery is to be mounted using a rotating laser beam that emits a rotating laser beam in an essentially horizontally plane. A photosensitive position sensor delivers an electrical pulse, which is identified by its timing and phase angle, during illumination by the laser beam. The phase angle and timing of these pulses constitute a measure of the position of the sensor in the coordinate system. Measurements are taken with the sensor positioned at each location at which the machinery is to be fixed to a factory floor. The method determines any differences in height between the measurement points and the amount, if any, that the floor needs to be adjusted at each mounting point to insure that a machine that is affixed to the floor these points will be level.

9 Claims, 2 Drawing Sheets

METHOD OF DETERMINING THE FLATNESS OF A FOUNDATION TO WHICH A BUILDING STRUCTURE, MACHINERY OR EQUIPMENT IS TO BE MOUNTED

BACKGROUND OF THE INVENTION

1. Field of the Invention

The invention relates to a method of using a laser-based position measuring device to determine the flatness of a foundation to which a structure, machinery or equipment is to be mounted. In particular, the invention relates to any situation where a building structure, machinery or equipment needs to be mounted in a level manner, such as a machine on a factory floor, particularly that of a newly built factory, a building on its foundation, a wind powered electrical generator on a mounting slab, etc. Thus, for purposes of this application, the term foundation should be viewed in its general sense as an underlying base or support, or a body or ground upon which something is built up or overlaid.

2. Description of Related Art

When installing machinery in a factory, especially in a newly built factory, before mounting of the machinery in place, e.g., by drilling holes to bolt down the feet of the machinery to the floor, it is necessary to know how much each foot will be higher or lower than a certain reference point since most factory floors are not perfectly level.

Position measuring devices are available in many types. One well-known type is known under the generic term "total station." A total station is combination of an electronic theodolite or transit and an electronic distance measuring (EDM) device with associated computer based software. Angles and distances from the instrument to points to be surveyed are measured, and the coordinates of the actual positions of the points are calculated.

Most total station instruments measure angles by electro-optical scanning of extremely precise digital bar-codes etched on rotating glass cylinders or discs within the instrument. Distance measurement is often accomplished with a modulated microwave or infrared carrier signal that is generated by a small solid-state emitter within the instrument's optical path and reflected from the object to be measured. The modulation pattern in the returning signal is read and interpreted by a computer associated with the total station. The speed-of-light lag between the outbound and return signal is translated into distance. Most total stations use a purpose-built glass prism as the reflector for the EDM signal and can measure distances out to a few kilometers. The reflector is typically held by a person at various positions in the survey while an operator operates the device. However, it is also possible to have robotically operated devices in which the operator can remotely control the machine, while holding the reflector. These devices are quite complex and are very expensive.

There is a need for a simpler, and thus less expensive alternative to mere trial and error adjustments during installation of factory floor mounted machinery.

SUMMARY OF THE INVENTION

An aspect of the invention is to provide a device that is more economical than the known devices and can be used for tasks, such as determining the flatness of a foundation to which a structure, machinery or equipment is to be mounted.

This object is achieved in accordance with the invention by a process in which markings for the feet of the machine are place on the floor with x-y coordinates of these markings being stored in a computer in a reference table, and a rotating laser and position sensor being used to produce signals with which the computer can calculate the height at the marked positions based on a comparison of the detected sensor positions and the values stored in the computer reference table for each of the marked positions.

These and other aspects of the invention will become apparent in view of the description and drawings below.

DETAILED DESCRIPTION OF THE INVENTION

Figure 1:
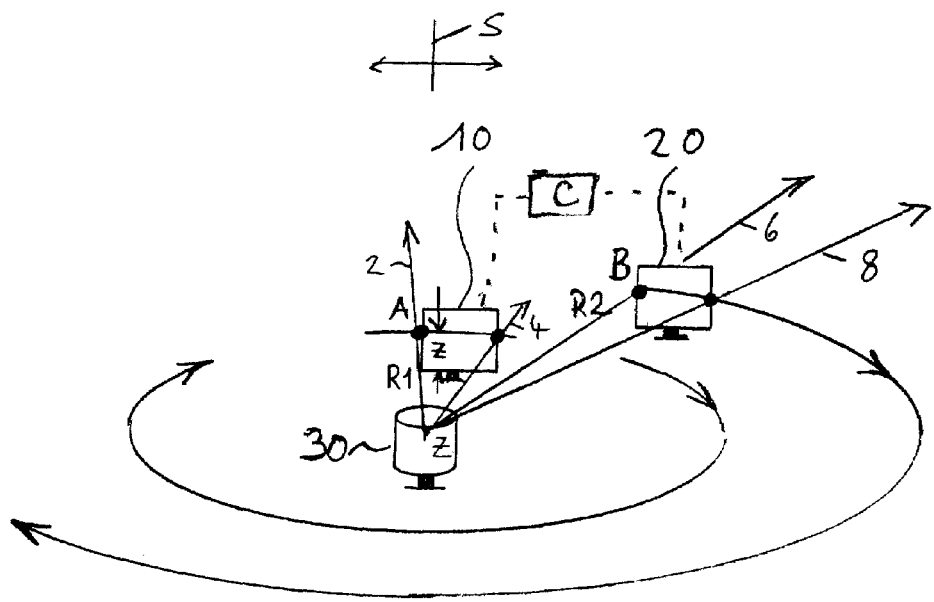
FIG. 1 is a schematic representation of a laser beam rotating in a horizontal plane generated from a device in accordance with the invention.

FIG. 1 schematically shows a laser beam that rotates in the horizontal plane AZB. To do this, a laser beam generator 30 is used that has a motorized means (not shown) with which a laser beam can be set into rotary motion around a central vertical axis Z. In this case, the laser beam moves successively into reference marked, mounting positions 2, 4, 6, and 8 (or however many positions at the machinery is to be fixed to the floor), which correspond the positions at which the legs of a piece of machinery that is to be installed on the factory floor are to be located in an essentially horizontally lying plane, which generally is parallel to the floor of the factory (which is almost never perfectly flat at the installation location). The motorized means is made such that a very constant angular velocity of the laser can be maintained so that, for example, the deviation of the laser beam from the actual angular position relative to the theoretical angular position at any given instant is simply, for example, $10E^{-4}$ rad (100 microrad). The components of such a motorized means are known. In times that periodically recur in an exact manner, the laser beam can therefore scan a position sensor 10, 20 at each referenced marked location.

Before the scanning with the laser beam is performed, it is necessary to determine the x- and y-coordinates of the position 2, 4, 6, 8 relative to the Z axis, and then to store these coordinates in a reference table in a computer. This can be done, for example, by placing a graduated ruler at a certain reference position, e.g., at the axis of rotation Z or at one of mounting positions 2, 4, 6, 8, and measuring how many units in x- and y-directions each of the position 2, 4, 6, 8 and the of the center of rotation of the laser is from the reference position. These x, y coordinate values are stored in a computer C. However, given the use of CAD to create blueprints, preferably, the x, y data sets in the computer will be generated, most of the time, by the program that produces the drawing for the layout of the factory, wind energy structure, etc. This same data set will serve two purposes. First, it will be used by the computer program driving the operation of the inventive measurement device. The second use will be as a list of positions for the person who walks with a tape measure and puts markings down where the sensor(s) is/are to be placed.

The measurement sensors 10, 20 can be optoelectric detectors, for example, such as a semiconductor position detector. The sensor is able to generate a signal based on the site on the sensor at which the laser beam impinges. A suitable signal is an electrical pulse identified by length of time and phase angle of the illumination by the laser beam. The signal can represent one-dimension, and preferably two-dimensions. In particular, the optoelectronic detector is relatively fast and within an extremely short time produces an output signal or an altered output signal as soon as light or additional light is incident on it.

According to the invention, the determination of the aforementioned x- and y-position is accomplished as follows. First, a radius angle determination is carried out in polar coordinates (rho, phi). The determined polar coordinates are then converted by electronics or a computer into an x- and y-position determination. The optoelectronic sensor of the invention therefore delivers signals which, depending on its position, have a different, but exactly definable phase angle that is determined, for example, by the rising edge of the measured pulse relative to cyclically repeated time zero points $t_{s1}$ and $t_{s2}$ which are stipulated on the laser beam generator (compare FIG. 2). Furthermore, according to the invention, the length in time of the signals delivered by the optoelectronic sensor is variable and depends essentially on the radial distance of the sensor from the center Z. If provisions are made for the receiving surface of the sensor to be oriented perpendicular to the incident laser beam, therefore, based on the length of a pulse in time and its phase angle, the coordination of the measurement point by radius and relative angle with respect to a starting angle can be undertaken.

Figure 2:
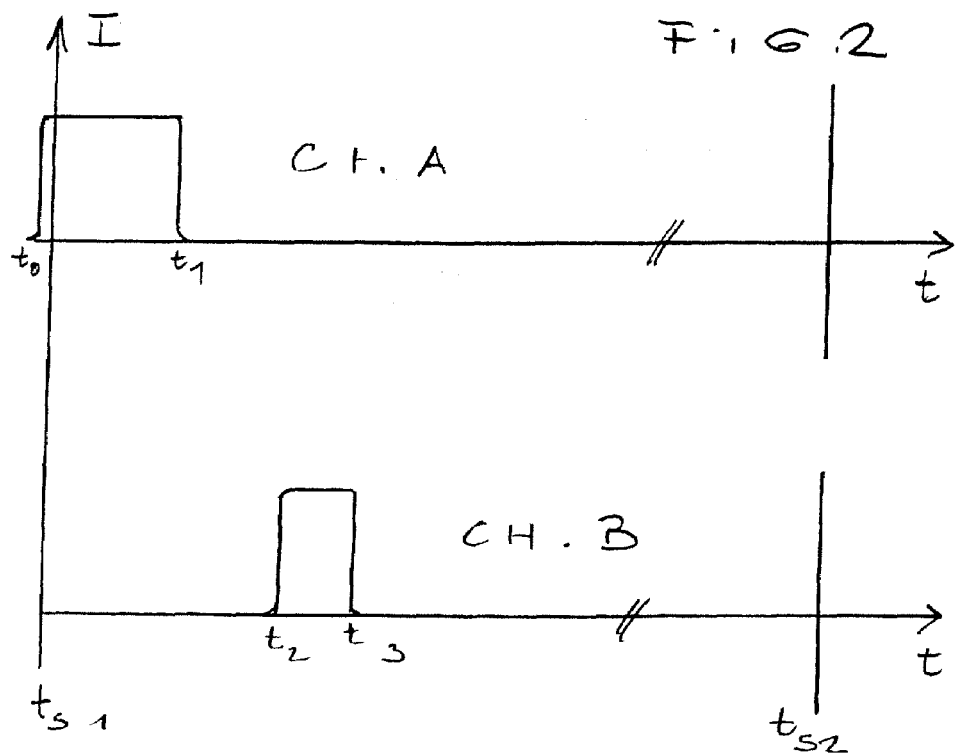
FIG. 2 is a plot of the laser pulses generated by a device in accordance with the invention.

For example, FIG. 1 shows a sensor 10 that is positioned at a radial distance R1 at position A, over which a laser beam generated by laser beam generator 30 is swung from the initial position 2 to the end position 4, at a height "z". As long as the sensor 10 is illuminated by the laser beam, at least one signal is delivered. However, the sensor 10 is devised such that, preferably, two signals can be delivered that contain information about the impact point of the laser beam according to two coordinates at positions 2 and 4. The time signal, which is present during illumination of the sensor 10 by the laser beam, is shown in FIG. 2 over the time between the instants $t_0$ and $t_1$ as a channel A ("CH.A"). A data processor, such as a computer C shown schematically in FIG. 1, with programmable circuitry or software based control system is in communication with the sensor 10 and, if desired, the generator 30 to receive and interpret the signals generated from the sensor 10 and, if desired, to control operation of the generator 30. The computer C can be coupled the sensor 10 and generator 30 in any known manner, especially in a wireless manner to facilitate an efficient measurement procedure.

If the same or a second sensor 20 is positioned at position B with a radial distance R2, the laser beam can illuminate it between the angular positions 6 and 8, beginning from position B, which can have a ordinate value different than that in position A. The respective delivered electrical pulse is shown in FIG. 2 in the lower part as a channel B signal ("CH.B") between the instants $t_2$ and $t_3$. The instants $t_2$ and $t_3$, therefore, in this example, are later than $t_0$ and $t_1$. The corresponding time difference of the pulse centers is therefore a measure of the angle AZB. Furthermore, the pulse widths ($t_0$–$t_1$) and ($t_2$–$t_3$) are different, due to the respectively identical measurement surface of the sensor 20 and the different radial distances in the different measurement positions. For a fixed sensor that remains in one position, comparable pulses arise with each beam passage so that data from several pulses, for example, 5 to 70 pulses, can be combined into a mean value. Such a mean value then has higher precision than only a single measurement value.

In addition to the data for its coordinates (by radius and azimuth angle), the sensor 10 can thus simultaneously deliver a leveling value (height value or z-component) to the controller C from the respective measurement position so that, with a small number of system components, an especially economical measuring device that measures in three dimensions is provided.

In this case, the relative flatness of a surface can be determined by using the position identified on the sensor 10 of the rotating horizontal laser beam to generate data relating to the relative height of the sensor. By positioning the sensor 10 at different points of the surface and taking measurements at these points, the laser beam will change its position on the sensor according to the deviation in relative height. The deviation at each measurement position thus provides data as to the relative flatness of a surface without the need to take extensive detailed measurements of angular displacement of beam with respect to the measurement device, as is required in the more complex prior art devices.

In operation, a grid of measurement points is defined across a coordinate system on the surface to the measured. The measurement points are established at predefined locations which need not necessarily be an evenly spaced pattern even though such is shown for the grid of FIG. 5. Each predefined location represents a point at which measurement will occur, i.e. where the sensor will be positioned. Then, the measurement process explained above is executed to determine the deviation and thus the relative flatness. One inherent inaccuracy that can occur with this method is imprecisely positioning the sensor with respect to the predefined target measurement point. To overcome this inherent issue, in accordance with this invention, the process can include an automatic self correcting function.

Figure 3:
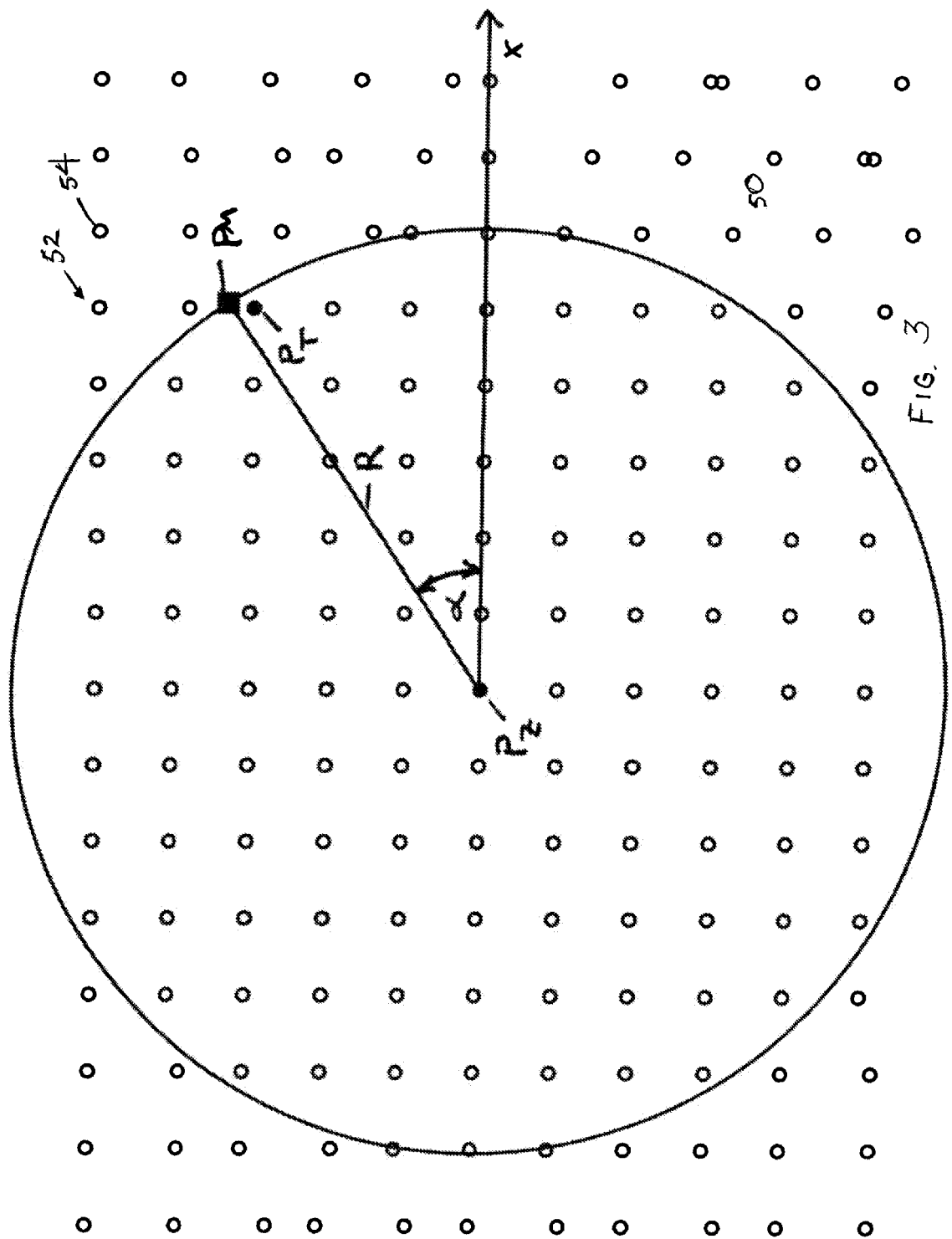
FIG. 3 is schematic diagram of a predefined coordinate grid showing an actual measurement point compared to a predefined target measurement point.

Referring to FIG. 3, a surface 50 to be measured for flatness is shown. A grid 52 of measurement coordinates 54 is defined on the surface 50. The coordinates of each point 54 of the grid 52 are stored in a data base accessible to the computer C, as seen in FIG. 1. The measurement device or laser beam generator 30 is positioned at a generally central point $P_Z$ and a measurement for the coordinate $P_M$ is taken by passing the laser beam over a sensor 10 at $P_M$, which generates a signal that corresponds to the absolute radial (R) value and the angular ($\alpha$) value with respect to the x-axis or plane.

The signal is provided to the computer C, which uses the measured values at point $P_M$ to determine the coordinates of the point $P_M$. The computer C recognizes that the coordinates of $P_M$ do not match the coordinates of the target measurement point $P_T$, by comparing the stored coordinates to the determined coordinates. The differences between the measured coordinates of point $P_M$ and the target coordinates of point $P_T$ are determined. The measured values are then adjusted using the determined differences so that the coordinates of $P_M$ correspond to the predefined target coordinates of $P_T$ from the grid 52. Thus, if the sensor 10 is not precisely positioned at the target measurement point, the system can accommodate the variance and correct the measured values.

Then to determine the relative flatness of the surface 50, the sensor 10 or another sensor 20 is positioned for the next measurement and the process is repeated, with the computer C making an adjustment for the predefined target measurement point and the actual measurement point. By this, any inaccuracies from positioning the sensor at a point other than on a point 54 on the predefined grid 52 can be automatically corrected. Thus, mispositioning the sensor can be accommodated to result in an assisted absolute measurement value.

In the preferred process of the invention, the position sensor(s) is/are placed device down as precisely as possible on the markings or measurement points. This may be helped by a fixture on the floor, to which the sensor foot can be fixedly attached. The sensor 10, 20 is aligned so that its sensitive surface will be hit by the laser beam perpendicular to its surface at the center. For example, if you want to measure a point on the x axis, you try to get the sensor as close as possible to being parallel to the yz-plane.

When the laser beam is being rotated, it scans the sensor 10, 20 and thus creates an electrical pulse. The difference between on and off times of this pulse is determined. This time difference is used to calculate the distance from the center of rotation of the laser beam, assuming the sensor size as a given. This center of rotation of the laser beam is also the origin of an rho, phi polar coordinate system. When measuring the first marking on the floor, which measurement point or marking the reading is being taken at is input into the computer, e.g., by entering x and y coordinates on a keyboard. Next, the height of the laser beam on the sensor 10, 20, i.e., the z value is read from the position sensor 10, 20.

From the second marking on, the computer will detect when the pulses are coming at a steady rate again. Thus, it will know that the sensor is no longer being moved around and decides the sensor has arrived at another measurement position. Alternatively, if multiple sensors are being used, the computer can be set to know the sensor sequence, i.e., the order in which each of the sensors will be illuminated by the rotating laser beam, e.g., 10, then 20 in the arrangement of FIG. 1.

Then, the computer will read the r coordinate again, i.e., the distance from the center of rotation of the laser beam for the second measurement point. The angle between 1st and 2nd measurement point phi in the rho, phi coordinate system is calculated with the help of a real time clock. If it is assumed that the laser is performing a full rotation in precisely 1.000000 second, and for the sake of simplicity, that the on time of the pulse of the sensor at the first measurement position coincides with the full second of the real time clock, when the computer detects the pulses coming at a steady rate again, it reads the r of the 2nd position as described above. Then, it starts comparing the on time of the pulses with the real time clock. If these pulses are coming, e.g., always at the full second plus 100 milliseconds, the computer will be able to calculate the angle between 1st and 2nd measurement points by multiplying the rotation rate of 1.000000 rotation per second with the 100 ms time difference for the 1st and 2nd measurement points to be a tenth of a full circle, i.e., 36°.

These values for radius rho and angle phi will be converted by the computer to x, y coordinates. Then, the sensor is carried to the 3rd position, or the computer can automatically switch a third sensor with which distance from the center of rotation of the laser beam (from pulse duration), angle relative to the 2nd position (from comparison with real time of onset of pulse) and height z (signal from the sensor) are measured and calculated again.

The above described steps are repeated until calculations have been completed for all of the markings. In this regard, it is possible to compare the calculated x, y coordinates with the coordinates stored in a reference table, so that the computer will be able to determine at which of the markings the sensor is positioned, with the computer making a z determination. In this manner, the computer will be able to automatically calculate a z reading for each measurement point at which the sensor is positioned.

The value of having a reference table with sets of x, y coordinates in the computer is that it allows the computer to "know" where the sensor(s) is/are likely to be, i.e., when the laser beam is likely to intercept a sensor. Without the reference table, all measurements will depend on each other and the errors of the individual measurements will add up over time. These errors will be reduced, if each measurement is taken at or near a previously known location.

The use of a reference table with sets of x and y coordinates is an advantage of the present invention when a wireless data transmission system, like Bluetooth® computer communication equipment, is used. In general, computer communications are facing the problem of synchronizing two devices in communication with each other. This problem is aggravated when wireless communication is being used. This is where the use of a reference table or at least a second sensor is advantageous. A reference table with a fixed set of possible positions of the sensor helps the computer to determine at which times to expected signals to come from the sensor or sensors. By keeping a second sensor in a fixed position, which may be input to the computer at the beginning of the measurement, the second sensor will give a known pulse timing at a known position. If the other sensor is being moved around, the second fixed sensor can and should be used as a reference point in the calculations of radius and angle.

Various modifications and changes may be made to the invention as set forth in the appended claims, including adding certain measuring and determination functions depending on the particular intended use. Also, different types of generators, sensors, and processors may be used.

What is claimed is:

1. A method for measuring flatness of a foundation to which a structure, machinery or equipment is to be mounted, comprising the steps of:

defining an x-, y-coordinate system;

determining x- and y-coordinates within the coordinate system of positions at which mounting points are to be located and storing the coordinates in a reference table in a computer;

generating and moving a laser beam in a horizontal plane in a manner which causes the laser beam to sequentially intercept each of the measurement points;

generating signals from a respective position sensor located at each measurement point based on illumination of the sensor by the laser beam;

determining coordinates of each of the measurement points from the signals generated by the respective position sensor and comparing the determined coordinates to the stored coordinates of the measurement points so as to match a height measurement obtained from a vertical position of impingement of the laser beam on the sensor at each measurement point with a particular measurement point; and determining the actual height of each of the measurement points from height measurements obtained as an indication of the flatness of the foundation;

wherein the coordinates determining step comprises using a time difference between when a single laser beam first enters and then leaves a detecting area of the respective position sensor at each of the measurement points in a calculation to determine the distance of each measuring point from the laser based upon the length of the detecting area in said horizontal plane.

2. The method as claimed in claim 1, comprising the further step of determining any required adjustments in height required at each of the mounting points for the structure, machinery or equipment to be levelly mounted when fixed to the foundation at said mounting points.

3. The method as claimed in claim 1, wherein the step of generating and moving the laser beam includes rotating the laser beam at a constant velocity said horizontal plane.

4. The method as claimed in claim 1, wherein the step of generating signals includes generating electric pulses.

5. The method as claimed in claim 3, wherein the generated signals are representative of a length in time and a phase angle of the laser beam.

6. The method as claimed in claim 5, wherein the coordinate determining step comprises converting radius and angle values into x- and y-coordinate values.

7. The method as claimed in claim 5, wherein the generated signals are also representative of a location of impingement on the sensor of the laser beam.

8. The method as claimed in claim 1, wherein the generated signals are representative of a location of impingement on the sensor of the laser beam.

9. The method as claimed in claim 1, wherein the step of generating the laser beam includes delivering a pulsed laser beam.

* * * * *

UNITED STATES PATENT AND TRADEMARK OFFICE
CERTIFICATE OF CORRECTION

| | |
|---|---|
| PATENT NO. | : 7,612,872 B2 |
| APPLICATION NO. | : 11/680952 |
| DATED | : November 3, 2009 |
| INVENTOR(S) | : Volker Konetschny and Klaus Stroel |

It is certified that error appears in the above-identified patent and that said Letters Patent is hereby corrected as shown below:

On the Title Page, Item (73) should read

(73) Assignee: Prueftechnik Dieter Busch AG, Ismaning (DE)

Signed and Sealed this
First Day of March, 2011

David J. Kappos
*Director of the United States Patent and Trademark Office*